United States Patent [19]
Belleau et al.

[11] Patent Number: 5,486,520
[45] Date of Patent: Jan. 23, 1996

[54] 1,3-OXATHIOLANES USEFUL IN THE TREATMENT OF HEPATITIS

[75] Inventors: Bernard Belleau, deceased, late of Quebec, by Pierrette Belleau, executrix; Nghe Nguyen-Ba, Quebec, both of Canada

[73] Assignee: BioChemPharma, Inc., Laval, Canada

[21] Appl. No.: 166,320

[22] Filed: Dec. 10, 1993

Related U.S. Application Data

[63] Continuation of Ser. No. 884,729, May 15, 1992, abandoned.

[30] Foreign Application Priority Data

May 20, 1991 [GB] United Kingdom .................. 9110874

[51] Int. Cl.$^6$ .................... A01N 43/54; A61K 31/505
[52] U.S. Cl. ............................. 514/274; 514/49
[58] Field of Search .................. 544/265, 276, 544/277, 313, 314, 317; 514/49, 262, 274, 45

[56] References Cited

U.S. PATENT DOCUMENTS

| | | | |
|---|---|---|---|
| 5,039,667 | 8/1991 | Tyrell et al. | 514/45 |
| 5,047,407 | 9/1991 | Belleau et al. | 514/274 |
| 5,151,426 | 9/1992 | Belleau et al. | 514/262 |
| 5,204,466 | 4/1993 | Liotta et al. | 544/317 |
| 5,210,085 | 5/1993 | Liotta et al. | 514/274 |

FOREIGN PATENT DOCUMENTS

| | | | |
|---|---|---|---|
| 0206497A2 | 12/1986 | European Pat. Off. | 31/70 |
| 0302760B | 6/1988 | European Pat. Off. | 31/70 |
| 0349242A2 | 1/1990 | European Pat. Off. | |
| 0382526A2 | 8/1990 | European Pat. Off. | |
| 0421777A1 | 4/1991 | European Pat. Off. | 19/67 |
| 0421739A1 | 4/1991 | European Pat. Off. | 31/70 |
| 0421819A1 | 4/1991 | European Pat. Off. | 405/4 |
| 0494119A1 | 7/1992 | European Pat. Off. | 31/505 |
| 0505181A1 | 9/1992 | European Pat. Off. | 31/70 |
| 2230266 | 10/1990 | United Kingdom | 19/4 |
| WO89/04662 | 6/1989 | WIPO | 31/66 |
| WO90/12023 | 10/1990 | WIPO | 19/10 |
| WO92/16215 | 10/1990 | WIPO | 31/70 |
| WO90/14079 | 11/1990 | WIPO | |
| WO90/14091 | 11/1990 | WIPO | 31/70 |
| WO91/00282 | 2/1991 | WIPO | 31/52 |
| WO91/01326 | 2/1991 | WIPO | 31/70 |
| WO91/01137 | 2/1991 | WIPO | 31/70 |
| WO91/11186 | 8/1991 | WIPO | 31/505 |
| WO91/17159 | 11/1991 | WIPO | 31/505 |
| WO92/08717 | 5/1992 | WIPO | |
| WO92/11852 | 7/1992 | WIPO | 31/505 |
| WO92/14743 | 9/1992 | WIPO | |
| WO92/15308 | 9/1992 | WIPO | 31/505 |
| WO92/18517 | 10/1992 | WIPO | 31/70 |
| WO92/19246 | 11/1992 | WIPO | 31/70 |

OTHER PUBLICATIONS

Coates et al., "The Separated Enantiomers of 2'-Deoxy-3'-Thiacytidine (BCH 189) Both Inhibit Human Immunodeficiency Virus Replication in Vitro," 36 *Antimicrobial Agents & Chemotherapy*, No. 1, pp. 202–205 (1992).

Doong et al., "Inhibition of the Replication of Hepatitis B Virus In–Vitro By 2'3' Dideoxy–3'–thiacytidine and Related Analogues," *Thirty-first Annual Interscience Conference of Antimicrobial Agents and Chemotherapy*, Chicago, Ill., USA, 29 Sep.–2 Oct. 1991, Program Abstract 31(0) 181 (1991).

Doong et al., "Inhibition of the Replication of Hepatitis B Virus in vitro by 2',3'–dideoxy–3'–thiacytidine and related analogues," 88 *Proc. Natl. Acad. Sci., USA*, pp. 8495–8499; 88 Physiology/Pharmacolgy 8495–99 (1991).

Greenberg et al., "Metabolism, Toxicity, and Anti–HIV Activity of 2'–Deoxy–3'–Thia–Cytidine (BCH–189) in T and B Cell Lines," 616 *Annals of the New York Academy Of Sciences* 517–18 (1990).

Kassianides et al. Abstract: "Effects of 2',3'–dideoxycytidine on Duck Hepatitis B Virus," 94 *Gastroenterology* No. 5, A552 (1988).

Kassianides et al., "Inhibition of Duck Hepatitis B Virus Replication by 2',3'–Dideoxycytidine," 97 *Gastroenterology*, No. 5, 1275–80 (1989).

Lee et al., "In Vitro and In Vivo Comparisons of the Abilities of Purine and Pyrimidine 2',3'–Dideoxynucleosides To Inhibit Duck Hepadnavirus," 33 *Antimicrobial Agents and Chemotherapy*, No. 3, 336–39 (1989).

Sandstrom et al., "Antiviral Therapy in AIDS: Clinical Pharmacological Properties and Therapeutic Experience to Date," 34 *Drugs*, pp. 372–390 (1987).

Soudeyns et al., "Anti–Human Immunodeficiency Virus Type 1 Activity and in Vitro Toxicity of 2'–Deoxy–3'–Thiacytidine (BCH–189), a Novel Heterocyclic Nucleoside Analog," 35 *Antimicrobial Agents and Chemotherapy*, No. 7, pp. 1386–1390 (1991).

Suzuki et al., "Inhibition of Hepatitis B Virus Replication By Purine 2',3'–Dideoxynucleosides," 156 *Biochemical and Biophysical Research Communications* 1144–51 (1988).

Varmus, "A Growing Role For Reverse Transcription," 299 *Nature*, pp. 204–205 (1982).

Wainberg et al., Abstract, "Anti–HIV–1 Activity, Toxicity And Pharmacokinetics of Totally Novel Nucleoside Analogs," M.C.P.63, V International Conference on AIDS, Montreal, Quebec, Canada, Jun. 4–9, 1989.

(List continued on next page.)

*Primary Examiner*—Jacqueline M. Stone
*Assistant Examiner*—Bruce R. Campbell
*Attorney, Agent, or Firm*—Fish & Neave; Leslie A. McDonnell; Gerald J. Flattmann, Jr.

[57] ABSTRACT

The present invention relates to the use of nucleoside analogues in the treatment of viral infections. More specifically it is concerned with the use of 1,3-oxathiolane nucleoside analogues in the treatment of hepatitis, in particular hepatitis B.

10 Claims, No Drawings

OTHER PUBLICATIONS

Wainberg et al., "Characterization Of AZT-Resistant Isolates Of HIV-1: Susceptibility To Deoxythiacytidine And Other Nucleosides," VI International Conference On AIDS, San Francisco, Calif., vol. 3, Abstract S.B.87, p. 117 (1990).

Beach et al., "Synthesis of Enantiomerically Pure (2'R, 5'S)-(-)-1-[2-(Hydroxymethyl) oxathiolan-5-yl]cytosine as a Potent Antiviral Agent Against Hepatitis B Virus (HBV) And Human Immunodeficiency Virus (HIV)," 57 *J. Org. Chem.*, pp. 2217-2219 (1992).

Belleau et al., "Design And Activity Of A Novel Class Of Nucleoside Analogs Effective Against HIV-1," Fifth International Conference On AIDS, Montreal, Canada, Abstract T.C.O.1 (1989).

Carlisle et al., "Cellular Pharmacology Of The Anti-HIV Agent BCH-189 (2'-Deoxy-3'-Thiacytidine) In Human Peripheral Blood Mononuclear Cells (PBMC)", *American Association For Cancer Research Proceedings,* 31 Abstract 2435 (1990).

Chang et al., "Deoxycytidine Deaminase-resistant Stereoisomer Is the Active Form of (±)-2', -3'-Diedeoxy-3'-thiacytidine in the Inhibition of the Hepatitis B Virus Replication," 267 *J. Biol. Chem.*, pp. 3938-3942 (1992).

1,3-OXATHIOLANES USEFUL IN THE TREATMENT OF HEPATITIS

This is a continuation of application Ser. No. 07/884,729, filed May 15, 1992, now abandoned, entitled 1,3-OXATHIOLANES USEFUL IN THE TREATMENT OF HEPATITIS.

The present invention relates to the use of nucleoside analogues in the treatment of viral infections. More specifically it is concerned with the use of 1,3-oxathiolane nucleoside analogues in the treatment of hepatitis, in particular hepatitis B.

Hepatitis B is a viral disease transmitted orally or parenterally by contaminated material such as blood and blood products, contaminated needles, sexually and vertically from infected or carrier mothers to their off-spring. In those areas of the world where the disease is common, vertical transmission at an early age results in a high proportion of infected individuals becoming chronic carriers of hepatitis B. There are an estimated 280,000,000 carriers of hepatitis B worldwide. At the present time there are no effective chemotherapeutic agents for the treatment of hepatitis B infections.

European patent publication 0382526A describes a series of 1,3-oxathiolane nucleoside analogues having antiviral activity, in particular activity against HIV, the causative agent of AIDS. We have now found that certain of the compounds described in EP 0382526A are active both in vitro and in vivo against the hepatitis B virus.

The invention accordingly provides, in a first aspect, a method for the treatment of an animal, including man, infected with the hepatitis B virus comprising the administration of an effective amount of a compound of formula (I) or a pharmaceutically acceptable derivative thereof

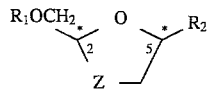

wherein $R_1$ is hydrogen or an acyl;
$R_2$ is a purine or pyrimidine base or an analogue or derivative thereof;
Z is S, S=O or $SO_2$;
provided that: $R_2$ is not cytosine when the compound of formula (I) is in the cis configuration, $R_1$ is hydrogen and Z is S.

It will be appreciated by those skilled in the art that the compounds of formula (I) contain at least two chiral centres (shown as * in formula (I)) and thus exist in the form of two pairs of optical isomers (i.e. enantiomers) and mixtures thereof including racemic mixtures. Thus the compounds of formula (I) may be either cis isomers, as represented by formula (II), or trans isomers, as represented by formula (III), or mixtures thereof. Each of the cis and trans isomers can exist as one of two enantiomers or as mixtures thereof including racemic mixtures. All such isomers and mixtures thereof including racemic mixtures are included within the scope of the invention:

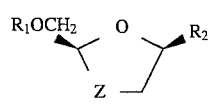

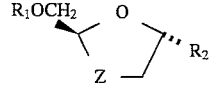

The compounds of formula (I) are preferably in the form of their cis isomers.

It will also be appreciated that when Z is S=O the compounds exist in two additional racemic forms as shown in formulas (IIa) and (IIb) which differ in the configuration of the oxide oxygen atom relative to the 2,5-substituents. The compounds of the invention additionally embrace such isomers and mixtures thereof.

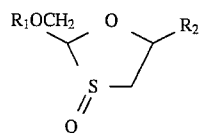

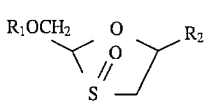

The purine or pyrimidine base $R_2$ will be linked at the 9- or 1- position respectively.

By purine or pyrimidine base or an analogue thereof is meant a purine or pyrimidine base found in nucleosides or an analogue thereof which mimics such bases in that their structures (the kinds of atoms and their arrangement) are similar to the normal bases but may either possess additional or lack certain of the functional properties of the normal bases. Such analogues include those derived by replacement of a $CH_2$ moiety by a nitrogen atom (for example, 5-azapyrimidines such as 5-azacytosine) or vice versa (for example 7-deazapurines, for example 7-deazadenosine or 7-deazaguanosine) or both (e.g. 7-deazadenosine or 7-deazaguanosine) or both (e.g. 7-deaza, 8-azapurines). By derivatives of such bases or analogues are meant those compounds wherein ring substituents are either incorporated, removed or modified by conventional substituents known in the art e.g. halogen, hydroxyl, amino, $C_{1-6}$ alkyl. Such purine or pyrimidine bases, analogues and derivatives will be well known to those skilled in the art.

Conveniently the group $R_2$ is selected from:

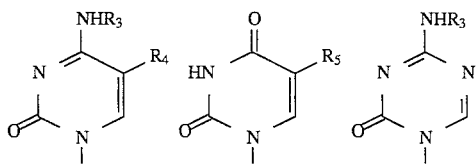

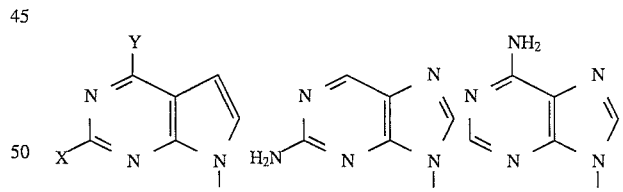

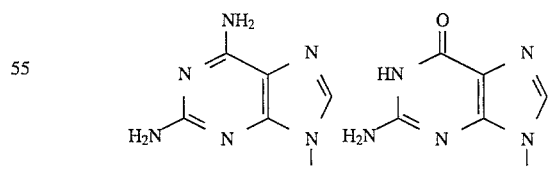

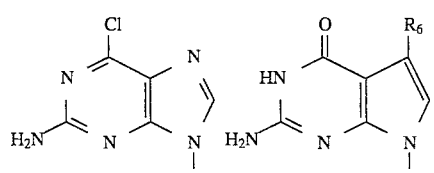

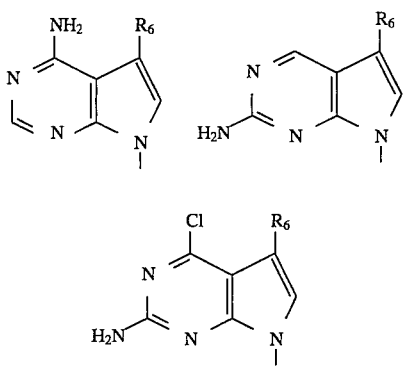

wherein $R_3$ is selected from the group consisting of: hydrogen and $C_{1-6}$ alkyl, unsubstituted or substituted with a heteroatom;

$R_4$ and $R_5$ are independently selected from the group consisting of: hydrogen, $C_{1-6}$ alkyl, bromine, chlorine, fluorine, and iodine;

$R_6$ is selected from the group consisting of: hydrogen, CN, carboxy, ethoxycarbonyl, carbamoyl and thiocarbamoyl; and X and Y are independently selected from the group consisting of: bromine, chlorine, fluorine, iodine, amino and hydroxy groups.

Preferably $R_2$ is

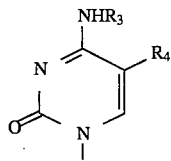

wherein $R_3$ and $R_4$ are as defined hereinabove.

Z is preferably —S—.

$R_3$ and $R_4$ are preferably hydrogen or $C_{1-6}$ alkyl.

$R_5$ is preferably $CH_3$ or F.

X and Y are preferably both $NH_2$.

It will be appreciated by one of skill in the art that when $R_1$ is an acyl group, the compounds of formula (I) are esters. Preferred esters include a carboxyl function R—CO—O in which the non-carbonyl moiety R is selected from hydrogen, straight or branched chain alkyl (e.g. methyl, ethyl, n-propyl, t-butyl, n-butyl), alkoxyalkyl (e.g., methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); substituted dihydro pyridinyl (e.g. N-methyldihydro pyridinyl); sulphonate esters such as alkyl- or aralkylsulphonyl (e.g. methanesulphonyl); sulfate esters, amino acid esters (e.g. L-valyl or L- isoleucyl) and mono-, di- or tri-phosphate esters.

Also included within the scope of such esters are esters derived from polyfunctional acids such as carboxylic acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters from the corresponding alcohol are well known. See, for example, Hahn et al., "Nucleotide Dimers as Anti Human Immunodeficiency Virus Agents", *Nucleotide Analogues*, pp. 156–159 (1989) and Busso et al., "Nucleotide Dimers Suppress HIV Expression In Vitro", *AIDS Research and Human Retroviruses*, 4(6), pp. 449– 455 (1988).

With regard to the above described esters, unless otherwise specified, any alkyl moiety present advantageously contains 1 to 16 carbon atoms, particularly I to 4 carbon atoms and could contain one or more double bonds. Any aryl moiety present in such esters advantageously comprises a phenyl group.

In particular the esters may be a $C_{1-16}$ alkyl ester, an unsubstituted benzoyl ester or a benzoyl ester substituted by at least one halogen (bromine, chlorine, fluorine or iodine), $C_{1-6}$ alkyl, saturated or unsaturated $C_{1-6}$ alkoxy, nitro or trifluoromethyl groups.

By the term "pharmaceutically acceptable derivative" is meant any pharmaceutically acceptable salt of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof, at functional groups in both the base moiety and at the $R_1$ group of the oxathiolane ring. Modifications at all such functional groups are included within the scope of the invention.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $NR_4+$ (where R is $C_{1-4}$ alkyl) salts.

References hereinafter to a compound according to the invention includes both the compound of formula (I) and its pharmaceutically acceptable derivatives.

Specific compounds of formula (I) include:

trans-2-hydroxymethyl-5-(cytosin-1'-yl)-1,3-oxathiolane;

cis-2-benzoyloxymethyl-5-(cytosin-1'-yl)-1,3-oxathiolane, trans-2-benzoyloxymethyl-5-(cytosin-1'-yl)-1,3-oxathiolane, and mixtures thereof;

cis-2-hydroxymethyl-5-($N_4$'-acetyl-cytosin-1'-yl)- 1,3-oxathiolane, trans-2-hydroxymethyl-5-($N_4$'-acetyl-cytosin- 1'-yl)-1,3-oxathiolane, and mixtures thereof;

cis-2-benzoyloxymethyl-5-($N_4$'-acetyl-cytosin-1'-acetyl-cytosin-1'-yl)-1,3-oxathiolane, trans-2-benzoyloxymethyl-5-($N_4$'-acetyl-cytosin-1'-yl)-3-oxathiolane, and mixtures thereof;

cis-2 benzoyloxymethyl-5-($N_4$'-acetyl-5-fluorocytosin-1'-yl)-1,3-oxathiolane, trans-2-benzoyl-oxymethyl-5-($N_4$'-acetyl-5-fluorocytosin-1'-yl)-1,3-oxathiolane, and mixtures thereof;

cis-2-hydroxymethyl-5-(5'-fluorocytosin-1'-yl)- 1,3-oxathiolane, trans-2-hydroxymethyl-5-(5'-fluorocytosin-1'-yl)-1,3-oxathiolane, and mixtures thereof;

cis-2-hydroxymethyl-5-(cytosin-1'-yl)-3-oxo-1,3-oxathiolane;

cis-2-hydroxymethyl-5-(thymin-N-1'-yl)-1,3-oxathiolane; and cis-2-hydroxymethyl-5-(N,N-dimethylaminomethylene-cytosin- 1'-yl)-1,3-oxathiolane;

in the form of a racemic mixture or a single enantiomer.

The compounds of formula (I) are preferably in the form of the cis compounds and contain two chiral centres (shown in formula (I) by *).

The compound of formula (I) is preferably in the form of a racemic mixture or a single enantiomer but a mixture of enantiomers in any ratio may be employed in the invention. Most preferably, the compound of formula (I) is in the form of its (−) enantiomer.

The compounds of formula (I) and their individual enantiomers may be prepared by any method known in the art for the preparation of compounds of analogous structure for example by the methods described in European patent publication 0382526A.

In a further or alternative aspect there is provided a compound of formula (I) as defined hereinabove or a pharmaceutically acceptable derivative thereof for use in the manufacture of a medicament for the treatment of hepatitis B.

As will be appreciated by those skilled in the art, references herein to treatment extend to prophylaxis as well as to the treatment of established infections of symptoms.

The compounds of formula (I) both as the racemic mixture and as the individual enantiomers have been found to inhibit the hepatitis B virus both in vitro and in vivo.

It will be appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or-dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or gum tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, nitrogen or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other antiinfective agents. In particular the compounds of the invention may be employed together with known antiviral, antibacterial, antifungal or immunomodulating agents.

The invention thus provides, in a further aspect, a combination comprising a compound of formula (I) or a physiologically acceptable derivative thereof together with another therapeutically active agent, in particular an antiviral, antibacterial, antifungal or immunomodulating agents.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The invention is illustrated by the following examples which should not be interpreted as a limitation of the invention.

EXAMPLE 1

Cis- and trans-2-benzoyloxymethyl-5($N_4$'-acetyl-5'-fluoro-cytosin-1'-yl)-1,3-oxathiolane 5-Fluorocytosine (4.30 g, 33.3 mmol), hexamethyldisilazane (25 ml) and ammonium sulfate (120 mg) were boiled under reflux until the cytosine dissolved (3 hours) and then further refluxed for 2 hours. The hexamethyldisilazane is evaporated in vacuo and toluene (100 ml) was added to the residue to co-evaporate the solvents. The resulting solution, bis(trimethylsilyl)-fluoro-cytosine in dichloromethane (40 ml) was added under argon to a solution of 2-benzoyloxymethyl- 5-acetoxy-1,3-oxathiolane (8,537 g, 30.3 mmol) in dry dichloromethane (100 ml) and molecular sieves (4A, 2 g) previously prepared under argon and cooled at 0° C. for 20 minutes. [(Trifluoromethane-sulfonyl)oxy]trimethylsilane (6 ml, 31 mmol) was added to this mixture at 0° C. and the resulting solution was stirred at 25° C. for approximately 18 hours. The reaction mixture was then treated with 300 ml of saturated solution of sodium bicarbonate and stirred at room temperature for 2 hours. The filtrate was shaken two times with 300 ml of brine and one time with distilled water. The organic layer was dried over magnesium sulfate, filtered and evaporated to dryness. This afforded a crude 5-fluorocytosine derivative (10.1 g). $R_f$:0.57 (EtOAc:MeOH 9:1).

This residue was acetylated in the next step without further purification. The crude material was dissolved in dry dichloromethane (120 ml) in a 500 ml round bottom flask under argon. Triethylamine (12.7 ml, 91.9 mmol) and dimethyl aminopyridine (111 mg, 0.9 mmol) were added to the solution. The flask was then immersed in an ice bath for i hour under argon. Acetic anhydride (4.3 ml, 45 mmol), distilled over sodium acetate, was syringed into the cooled flask. The mixture was stirred overnight and then carefully decanted into an erlenmeyer flask containing saturated sodium bicarbonate solution. The product was then washed with distilled water followed by brine solution. The methylene chloride portions were dried and evaporated under high vacuum to dryness, yielding an acetylated α/β mixture as a colorless foam, weighing 9.6 g after drying. Flash chromatography of this material using ethylacetate:methanol (9:1) afforded 3.1 g, 7.8 mmol (46%) pure trans-(benzoyloxymethyl-5-($N_4$'-acetyl- 5'-fluoro-cytosin-1'-yl) -1,3-oxathiolane) and 3.5 g, 8.9 mmol (30%) pure cis-(benzoyloxymethyl-5-($N_4$'-acetyl-5'-fluoro-cytosin-1'-yl)-1, 3-oxathiolane).

trans-isomer: $R_f$:0.65 in ethyl acetate:methanol 9:1
U.V.: (MeOH) Lambda max: 309 nm
$^1$H-NMR δ (ppm in $CDCl_3$)

8.77 (b, 1H; $C_4$'-N$\underline{H}$-Ac)

8.06 (m, 2H; aromatic)

7.70 (d, 1H; $C_6$'-$\underline{H}$, $J_{6',F}$=6.3 HZ)

7.62 (m, 1H; aromatic)

7.49 (m, 2H; aromatic)

6.51 (dd, 1H; $C_5$–$\underline{H}$)

5.91 (dd, 1H; $C_2$–$\underline{H}$)

4.48 (dd, 2H; $C_2$–C$\underline{H}_2$OCOC$_6$H$_5$)

3.66 (dd, 1H; $C_4$–$\underline{H}$)

3.34 (dd, 1H; $C_4$–$\underline{H}$)

2.56 (s, 3H; NH–CO$\underline{C}$H$_3$)

cis-isomer: $R_f$:0.58 in ethyl acetate:methanol 9:1
U. V.: (MeOH) Lambda max: 309nm
$^1$H-NMR δ (ppm in $CDCl_3$)

8.72 (b, 1H; $C_4'$-N$\underline{H}$-Ac)
8.06 (m, 2H; aromatic)
7.87 (d, 1H; $C_6'$-$\underline{H}$, $J_{6F}$=6.2 Hz)
7.60 (m, 1H; aromatic)
7.49 (m, 2H; aromatic)
6.32 (dd, 1H; $C_5$-$\underline{H}$)
5.47 (dd, 1H; $C_2$-$\underline{H}$)
4.73 (dd, 2H; $C_2$-$\underline{CH_2}$OCOC$_6$H$_5$)
3.62 (dd, 1H; $C_4$-$\underline{H}$)
3.19 (dd, 1H; $C_4$-$\underline{H}$)
2.55 (s, 3H; NH-$\underline{COCH_3}$)

EXAMPLE 2

Cis- and trans-hydroxymethyl-5-(5'-fluorocytosin-1'-yl)-1,3-oxathiolane 1.0 g (2.54 mmol) of trans-2-benzoyloxy-methyl- 5-($N_4'$-acetyl-5'-fluorocytosin-1'-yl)-1,3-oxathiolane was stirred in 25 ml of methanolic ammonia at 0° for 1 hour and then overnight at room temperature. The mixture was evaporated under reduced pressure. The residue as triturated twice (2×30 ml) with anhydrous ether. The solid residue was recrystallized in absolute ethanol to give 484 mg (1.95 mmol, 77%) of desired product trans-(hydroxymethyl-5-(5'-fluorocytosin-1'-yl) -1,3-oxathiolane): m.p. 219°– 221° C.; $R_f$=0.21 in ethyl acetate: methanol (9:1), which was identified by $^1$H, $^{13}$C-NMR and U.V. Lambda max (H$_2$O) 280.9 nm.

1.2 g (3.05 retool) of cis-2-benzoyloxymethyl- 5- ($N_4'$-acetyl-5'-fluoro-cytosin-1'-yl)-1,3-oxathiolane was stirred in 30 ml of methanolic ammonia at 0° C. for 1 hour and then overnight at room temperature. The mixture was evaporated under reduced pressure. The residue was triturated twice (2×30 ml) with anhydrous ether. The solid residue was recrystallized in absolute ethanol to give 655 mg (2.64 mmol, 87%) of pure product cis- (hydroxymethyl-5-(5'-fluorocytosin- 1'-yl)-1,3-oxathiolane): m.p. 204°–206° C.; $R_f$=0.21 in ethylacetate: methanol (9: 1). The desired compound was identified by $^1$H, $^{13}$C-NMR and U.V. Lambda max (H$_2$O) 280.9 nm.

trans- isomer:
$^1$H-NMR δ (ppm in DMSO-d$_6$):
7.85 (d, 1H; $C_6'$-$\underline{H}$, $J_{CF}$=7.01 HZ)
7.83 (d, 2H; $C_4'$-$\underline{NH_2}$)
6.30 (dd, 1H; $C_5$-$\underline{H}$)
5.60 (t, 1H; $C_2$-$\underline{H}$)
5.18 (t, 1H; $C_2$-$\underline{CH_2}$-OH)
3.49 (m, 3H; $C_2$-$\underline{CH_2OH+C_4H}$)
3.17 (dd, 1H; $C_4$-$\underline{H}$)
$^{13}$CNMR (DMSO-d$_6$), (Varian XL 300); δ in ppm

| $C_2'$ | $C_4'$ | $C_5'$ | $C_6'$ |
|---|---|---|---|
| 153.47 | 158.20 | 134.65 | 126.24 |
| ($^2J_{CF}$ = 13.2 Hz) | | ($J_{CF}$ = 26.2 Hz) | ($^2J_{CF}$ = 32.0 Hz) |
| $C_5$ | $C_4$ | $C_2$ | $CH_2OH$ |
| 88.20 | 36.18 | 87.16 | 64.71 | cis-isomer:
$^1$H-NMR δ (ppm in DMSO-d$_6$):
8.22 (d, 1H; $C_6'$-$\underline{H}$, $J_{CF}$=7.26 Hz)
7.843 (d, 2H; $C_4'$-$\underline{NH_2}$)
6.16 (t, 1H; $C_2$-$\underline{H}$)
5.43 (t, 1H; $C_2$-$\underline{CH_2}$-OH)
5.19 (t, 1H; $C_2$-$\underline{H}$)
3.77 (m, 2H; $C_2$-$\underline{CH_2OH}$)
3.35 (dd, 1H; $C_4$-$\underline{H}$)
3.12 (dd, 1H; $C_4$-$\underline{H}$)
$^{13}$CNMR (DMSO-d$_6$)

| $C_2'$ | $C_4'$ | $C_5'$ | $C6'$ |
|---|---|---|---|
| 153.46 | 158.14 | 134.63 | 126.32 |
| | ($^2J_{CF}$ = 14.0 Hz) | ($J_{CF}$ = 24.1 Hz) | ($J_{CF}$ = 32.5 Hz) |
| $C_5$ | $C_4$ | $C_2$ | $CH_2OH$ |
| 86.82 | 36.80 | 86.77 | 62.32 |

EXAMPLE 3

Biological Results (A) Newborn ducklings were infected with duck hepatitis B virus (DHBV). After 5 to 7 days post-infection, samples of blood were taken from the ducklings and examined for DHBV DNA using dot hybridization with a specific DNA probe (Mason et al., *Proc. Natl. Acad. Sci. USA* 79, pp. 3997–4001 (1982)). The livers were removed from dot-blot positive ducklings and used to produce primary hepatocyte cultures infected with DHBV as previously described (Tuttleman et al., *J. of Virology*, 58, pp. 17–25). After 2 days in culture, antiviral agents were added to the culture media. The media were changed every 2 days and at selected times, the cells were removed and the total DNA extracted.

The DNA was spotted on nitrocellulose paper and probed with the $^{32}$P-labelled DHBV DNA probe in accordance with the following procedure. The DNA from DHBV-infected hepatocytes was extracted and spotted onto a nitrocellulose filter. The above described $^{32}$P-nick translated-DHBV DNA (pDH-010=DHBV) probe was used. The DNA was extracted from 6-cm cell culture dishes at various times post-plating. In the virus control (VC) group, cells were harvested at 2, 6, 8, 10, 14, 18 and 20 days. Duplicate samples were spotted for days 14, 18 and 20. In drug-treated groups, cells were harvested on days 8, 14 and 20. Drugs were added to the culture at 2 days post-plating and maintained throughout media changes every 2 days. The total intracellular DNA was extracted from cells using the standard phenol extraction method. The cells in a 6-cm diameter Petri dish (approximately 5×10$^6$ cells) were lysed in a lysis buffer containing 0.2% SDS, 150 mM Tris-HCl pH 8.0, 10 mM EDTA, 5 mM EGTA, and 150 mM NaCl. The cell lysate was digested with 0.5 mg/ml of pronase E (available from Sigma) at 37° C. for 2 hours and proteinized by extraction with an equal volume of phenol saturated with 20 mM Tris-HCl, pH 7.5, 0.5 mM EDTA and 0.1% 8-hydroxyquinoline. Concentrated ammonium acetate (pH 7.0 (2.5M)) was added to the aqueous phase to yield a 0.25M ammonium acetate solution and the nucleic acids were precipitated with 2 volumes of 100% ethanol. The pellet of nucleic acid was washed with ethanol and dried. The DNA was dissolved in a solution containing 12.5 mM Tris-HCl, pH 7.5, 10 mM EDTA, 30% glycerol and 0.01% bromophenol blue. One twelfth of the DNA sample was spotted onto the nitrocellulose for dot-blot analysis.

The drugs tested were scored on a scale of 0 (no activity) to ++++ (high activity).

The compounds tested were 1,3 oxathiolanes and two known inhibitors of hepatitis B, 2', 3'-dideoxy-guanosine (ddG) and 2,6-diaminopurine-9-β-D- 2', 3'-dideoxyribofuranoside (ddDAPR)-(European Patent publication 0302760A).

The results are shown in Table 1.

TABLE 1

| Compound | Activity |
| --- | --- |
| trans-2-hydroxymethyl-5-(5'-fluorocytosin-1'-yl)-1,3-oxathiolane | + |
| cis-2-hydroxymethyl-5-(5'-fluorocytosin-1'-yl)-1,3-oxathiolane | +++ |
| cis-2-hydroxymethyl-5-(thymin-N-1'-yl)-1,3-oxathiolane | ++ |
| cis-2-hydroxymethyl-5-(N,N-dimethylaminomethylene cytosin-1'-yl)-1,3-oxathiolane | ++++ |
| ddG | ++++ |
| ddDAPR | ++++ |

What is claimed is:

1. A method for the treatment of hepatitis B infections in animals, including humans, comprising the step of administering, in an amount effective to inhibit viral replication, a compound selected from the group consisting of cis-2-hydroxymethyl-5-(5'-fluorocytosin-1'-yl)-1,3-oxathiolane;

trans-2-hydroxymethyl-5-(5'-fluorocytosin-1'-yl)-1,3-oxathiolane; and mixtures thereof;

or pharmaceutically acceptable derivatives thereof.

2. A method for the treatment of hepatitis B infections in animals, including humans, comprising the step of administering, in an amount effective to inhibit viral replication, cis-2-hydroxymethyl-5-(5'-fluorocytosin-1'-yl)- 1,3-oxathiolane or a pharmaceutically acceptable derivative thereof.

3. The method according to claim 1 or claim 2 wherein the compound is present as a single enantiomer or as a racemic mixture.

4. The method according to claim 1 or claim 2 wherein the compound is present as its (−) enantiomer.

5. The method according to claim 1 or claim 2 wherein the compound is present as its (+) enantiomer.

6. The method according to claim 1 or claim 2 wherein the compound is adapted for oral, parenteral, rectal, nasal, vaginal, or topical administration.

7. The method according to claim 1 or claim 2 wherein the compound is administered at a dose of about 0.1 to 750 mg/kg of bodyweight per day.

8. The method according to claim 7 wherein the compound is present in dosage unit form in the medicament.

9. The method according to claim 8 wherein the dosage unit form contains approximately 10 to 1500 mg of the compound.

10. The method according to claim 1 or claim 2 wherein the compound is administered with a pharmaceutically acceptable carrier.

* * * * *

UNITED STATES PATENT AND TRADEMARK OFFICE
CERTIFICATE OF CORRECTION

PATENT NO. : 5,486,520          Page 1 of 2
DATED      : January 23, 1996
INVENTOR(S): Belleau et al.

It is certified that error appears in the above-indentified patent and that said Letters Patent is hereby corrected as shown below:

| Column | Line | |
|---|---|---|
| 1 | 7 | "BioChemPharma, Inc." should be -- BioChem Pharma, Inc. -- |
| 1 | 36 | "2230266" should be -- 2230266A -- |
| 2 | 15 | "Physiology/Pharmacolgy" should be -- Physiology/Pharmacology -- |
| 2 | 20 | Insert a comma -- , -- after "et al." |
| 2 | 49 | "Campbell" should be -- Campell -- |
| 4 | 3 | "I" should be -- 1 -- |
| 4 | 50-51 | Delete first "-acetyl-cytosin-1'" |
| 4 | 52 | Insert -- 1, -- after "($N_4'$-acetyl-cytosin-1'-yl)-" |
| 5 | 46 | "I" should be -- 1 -- |
| 8 | 4 | Insert a hyphen -- - -- after "5" |
| 8 | 15 | "8,537" should be -- 8.537 -- |
| 8 | 33 | "i" should be -- 1 -- |
| 8 | 54 | "HZ" should be -- Hz -- |

UNITED STATES PATENT AND TRADEMARK OFFICE
CERTIFICATE OF CORRECTION

PATENT NO. : 5,486,520
DATED : January 23, 1996
INVENTOR(S) : Belleau et al.

It is certified that error appears in the above-indentified patent and that said Letters Patent is hereby corrected as shown below:

| Column | Line | |
|--------|------|---|
| 9 | 25 | "as" should be -- was -- |
| 9 | 34 | "retool" should be -- mmol -- |
| 9 | 48 | "HZ" should be -- Hz -- |
| 10 | 2 | "$C_2$" should be -- $C_5$ -- |
| 12 | 21 | "the" before "medicament" should be -- a -- |

Signed and Sealed this

Twenty-seventh Day of August, 1996

Attest:

BRUCE LEHMAN

*Attesting Officer*  *Commissioner of Patents and Trademarks*

UNITED STATES PATENT AND TRADEMARK OFFICE
Certificate

Patent No. 5,486,520                                                           Patented: January 23, 1996

On motion pursuant to 35 U.S.C. § 1.634 in Interference No. 104,019, it has been found that the above-identified patent, through error and without any deceptive intention, incorrectly sets forth the inventorship.

Accordingly, pursuant to 35 U.S.C. § 256 it is hereby certified that the correct inventorship of this patent is: Bernard Belleau, deceased by Pierrette Belleau, Nghe Nquyen-Ba, Gervais Dionne and Boulos Zacharie.

Signed and Sealed this Thirteenth Day of June, 2000.

MARY F. DOWNEY
*Administrative Patent Judge*
Board of Appeals and Interferences